United States Patent [19]

Spievack

[11] Patent Number: 5,350,379
[45] Date of Patent: Sep. 27, 1994

[54] BONE AND TISSUE LENGTHENING DEVICE

[75] Inventor: Alan R. Spievack, Watertown, Mass.

[73] Assignee: Genesis Orthopedics, Cambridge, Mass.

[21] Appl. No.: 18,820

[22] Filed: Feb. 18, 1993

[51] Int. Cl.⁵ .............................................. A61B 17/56
[52] U.S. Cl. .................................................... 606/63
[58] Field of Search ................ 606/63, 68, 60, 62, 606/64; 623/26, 38

[56] References Cited

U.S. PATENT DOCUMENTS

| | | |
|---|---|---|
| 3,976,060 | 8/1976 | Hildebrandt et al. . |
| 3,977,398 | 8/1976 | Burstein . |
| 3,986,504 | 10/1976 | Avila . |
| 4,091,806 | 5/1978 | Aginsky . |
| 4,157,715 | 6/1979 | Westerhoff .................... 606/63 X |
| 4,190,044 | 2/1980 | Wood . |
| 4,204,531 | 5/1980 | Aginsky . |
| 4,453,539 | 6/1984 | Raftopoulos et al. . |
| 4,522,200 | 6/1985 | Stednitz . |
| 4,615,338 | 10/1986 | Ilizarov et al. . |
| 4,854,312 | 8/1989 | Raftopoulos et al. . |
| 4,875,474 | 10/1989 | Border . |
| 4,940,467 | 7/1990 | Tronzo . |
| 4,946,459 | 8/1990 | Bradshaw et al. . |
| 5,002,543 | 3/1991 | Bradshaw et al. .................... 606/62 |
| 5,014,719 | 5/1991 | McLeod .............................. 128/774 |
| 5,034,012 | 7/1991 | Frigg ..................................... 606/62 |
| 5,034,013 | 7/1991 | Kyle et al. ............................ 606/62 |
| 5,057,103 | 10/1991 | Davis .................................... 606/63 |
| 5,059,193 | 10/1991 | Kuslich ................................. 606/61 |
| 5,071,435 | 12/1991 | Fuchs et al. .......................... 623/16 |
| 5,074,882 | 12/1991 | Grammont et al. .................. 623/23 |
| 5,102,413 | 4/1992 | Poddar .................................. 606/62 |
| 5,112,333 | 5/1992 | Fixel ...................................... 606/62 |
| 5,116,335 | 5/1992 | Hannon et al. ....................... 606/62 |
| 5,122,141 | 6/1992 | Simpson et al. ...................... 606/62 |
| 5,156,605 | 10/1992 | Pursley et al. . |
| 5,236,460 | 8/1993 | Barber ................................... 623/26 |

FOREIGN PATENT DOCUMENTS

4027183A1 8/1990 Fed. Rep. of Germany .
1091921 5/1984 U.S.S.R. ................................ 606/63

OTHER PUBLICATIONS

J. Götz and W. D. Schellmann, "Continuous Lengthening of the Femur by Intramedullary Stabilization", Archiv orthopädische Unfall–Chirugie 82:305–130 91975), copyright by J. F. Bergmann Publishing, Munich 1975. (In English and German).

Primary Examiner—Tamara L. Graysay
Attorney, Agent, or Firm—Hamilton Brook, Smith & Reynolds

[57] ABSTRACT

A device for lengthening bone in an human or animal by incrementally extending the distance between discrete separated portions of the bone to permit continued bone growth between the separated portions comprising an intramedullary nail having distal and proximal portions both of which are secured with the medullar canal of the bone. A hydraulic cylinder comprises the proximal portion of the nail and a piston comprises the distal portion of the nail. An implantable supply of operating fluid communicates with the cylinder. A ratcheting mechanism, between the piston and cylinder, limits their relative movement. A shock absorber mechanism permits limited lost motion between the piston and cylinder and ratcheting release mechanisms are employed to permit the piston and cylinder to reverse directions.

15 Claims, 6 Drawing Sheets

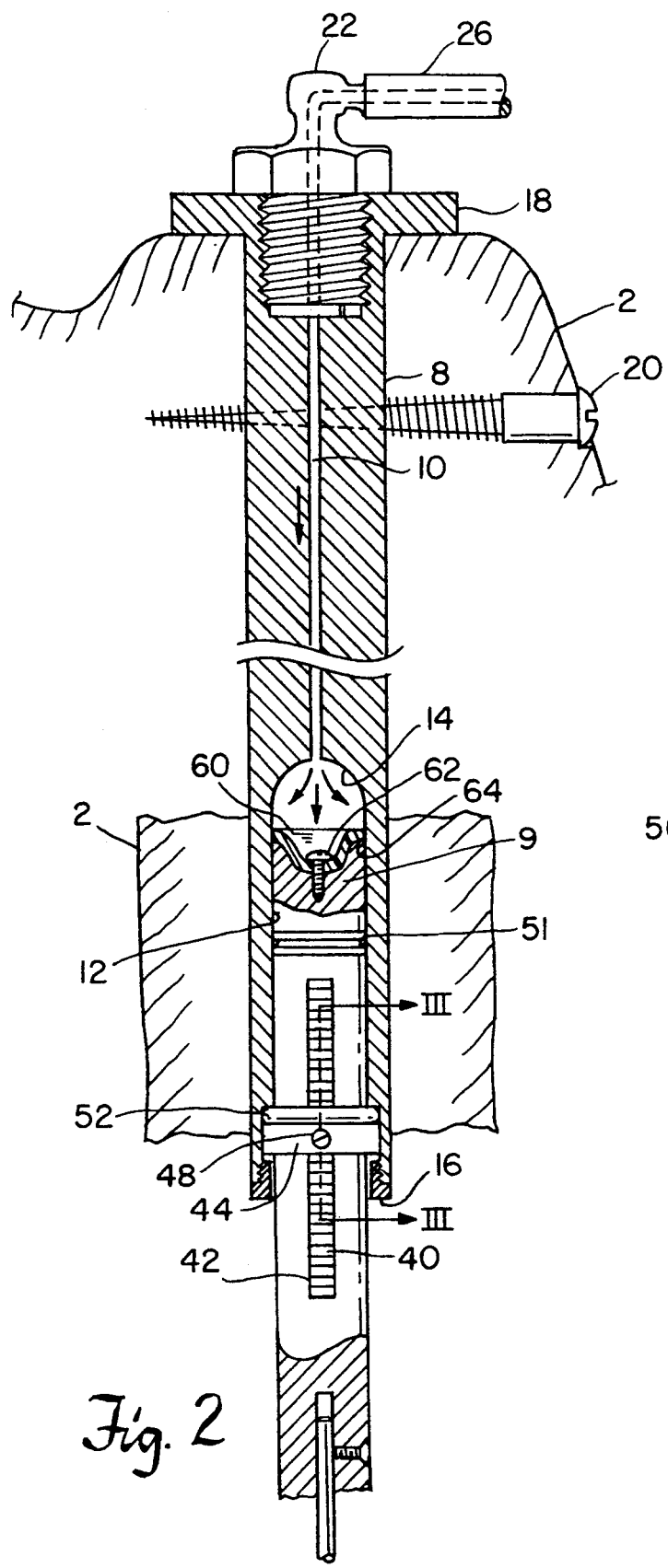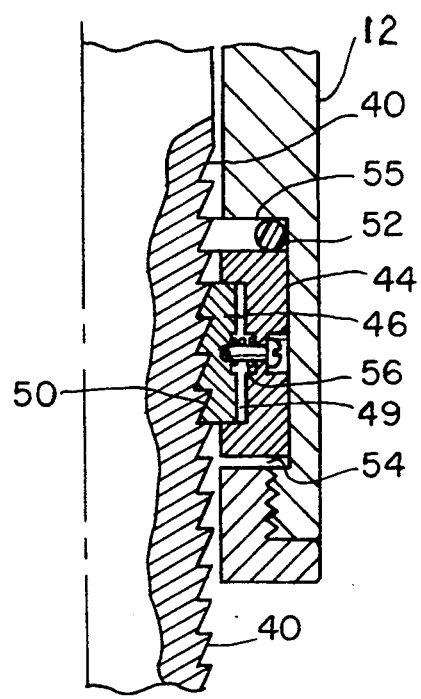
Fig. 2
Fig. 3

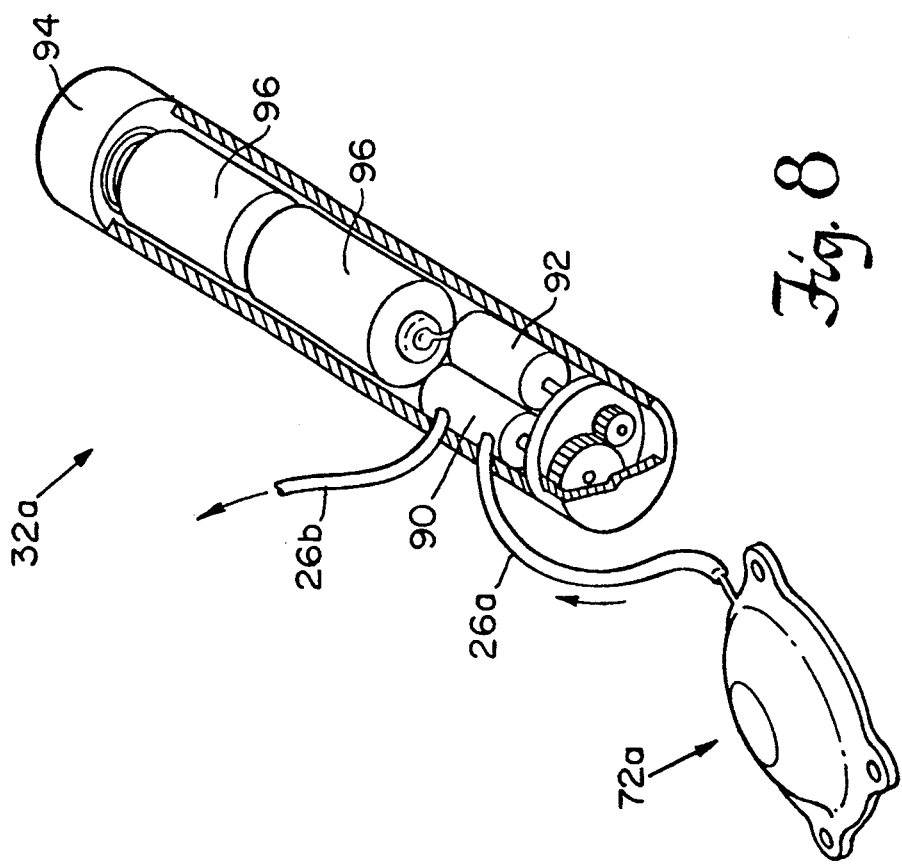
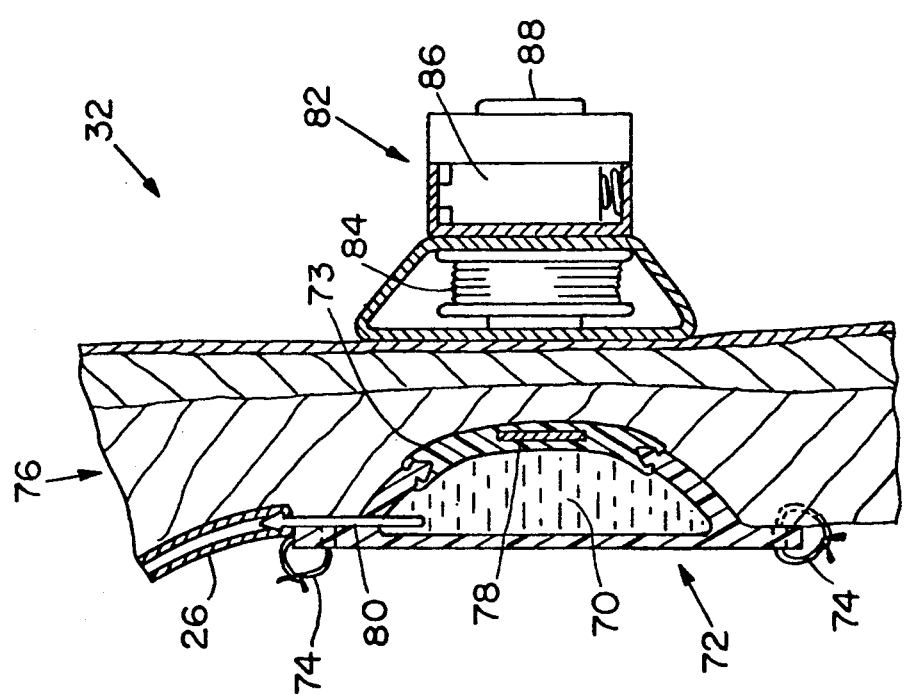

BONE AND TISSUE LENGTHENING DEVICE

BACKGROUND OF THE INVENTION

This invention pertains to apparatus for extending or lengthening bones and is particularly applicable to lengthening of human bones. There are many instances where a human being has one limb, particularly a leg, which is shorter than the other which could be congenital or due to an accident. It has been found possible to lengthen the deformed or shortened limb by devices which extend a proximal portion of a bone which has been severed from a distal portion. Such devices move the distal portion of the bone away from the proximal portion in small increments. This involves extending the gap between the severed bone portions in increments of approximately ¼ mm at a time. When the bones are thus separated, new bone tissue grows in the extended gap as well as soft tissue surrounding the bone. It is possible to lengthen a bone such as a femur 10 or more centimeters over a period of a few months.

One such device was developed in the USSR by Gavriil A. Ilizarov et al. which essentially is an extendable cage which fits externally around a limb. The distal end of the cage is incrementally extended from the proximal portion mechanically. One of the problems with this type of device is that a plurality of pins are inserted through the muscle of the limb, and into both portions of the bone. With the proximal portion of the limb "anchored" by the pins in the cage, force is transmitted through the pins to pull the distal portion away from the anchored portion. Such a device is described in U.S. Pat. No. 4,615,338. One of the problems created by this type of device is that numerous incisions are created in a limb by the pins which are susceptible to infection and that the pins are continually pulling on the flesh. Another disadvantage is that the wearing of a cage over a period of months severely limits the mobility of the patient.

Numerous other devices employ an elongated rod or nail known as an intramedullary rod or nail. Such devices are inserted into the marrow cavity or medullary passage of the bone. These rods are often threaded and are anchored to the bone from within the medullar canal and are incrementally moved by nuts or rachet means to incrementally continue separating bone portions. One such early device is shown in U.S. Pat. No. 3,986,504 to Avila. The racheting or extending of the threaded rod is accomplished externally by racheting mechanism or wrenches. Again, this type of device lends itself to infection.

Other types of devices have been developed also in the USSR by Alexander Bliskunov and employ racheting devices which are implanted internally and are operated by the patient himself who moves portions of his body to activate the racheting mechanism. One problem with this type of device is that accidental movement or excessive movement can cause too much bone separation, disturbing the growth pattern. It is to these problems that the present invention is directed. Another objective is to provide a completely implantable, hydraulically operated mechanism with as little opportunity for infection as possible and which is substantially foolproof in operation.

SUMMARY OF THE INVENTION

A device for lengthening bone and tissue in a human or animal is disclosed for incrementally extending the distance between discrete separated portions of the bone to permit continued growth between the separated portions. It includes an intramedullary nail having a distal portion and a proximal portion. The proximal portion of the nail is secured within the intramedullary canal of the bone at the proximal end thereof and the distal portion of the nail is secured within the intramedullary canal at the distal end thereof. A hydraulic cylinder is connected to the proximal portion and a piston moveable in the cylinder is connected to the distal end of the nail. There is an implantable supply of operating fluid in communication with the cylinder and racheting mechanism is located between the proximal and distal portions of the nail, i.e., the piston and cylinder, to limit their relative movement to one direction.

An alternative racheting mechanism, however, permits the proximal and distal portions of the nail (i.e., piston and cylinder) to reverse directions when the pressure of the operating fluid is released.

A shock absorbing member is interposed between the piston and the cylinder and cooperates with lost motion mechanism to provide a small amount of buffered lost motion, creating an environment to enhance growth between the separated portions.

The pressurizable fluid is contained in an implantable reservoir which may be pumped either manually or from an external signalling device or an internal pump controlled by an implantable battery operated microprocessor.

It will be understood that the device, while illustrated as lengthening the femur, can with simple modification be adjusted to lengthen all long bones.

The above and other features of the invention, including various novel details of construction and combinations of parts will now be more particularly described with reference to the accompanying drawings and pointed out in the claims. It will be understood that the particular bone and tissue lengthening device embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 2 is a detail view of an upper portion of the device shown in FIG. 1.

FIG. 3 is a detailed sectional view on an enlarged scale taken on the lines III—III of FIG. 2 of rachet means for limiting movement of the device shown in FIG. 1.

FIG. 7 is a detail view of means for supplying presurized operating fluid to the device.

FIG. 8 is an alternative embodiment of the means for supplying pressurized operating fluid.

DETAILED DESCRIPTION OF THE INVENTION

Figure 1:
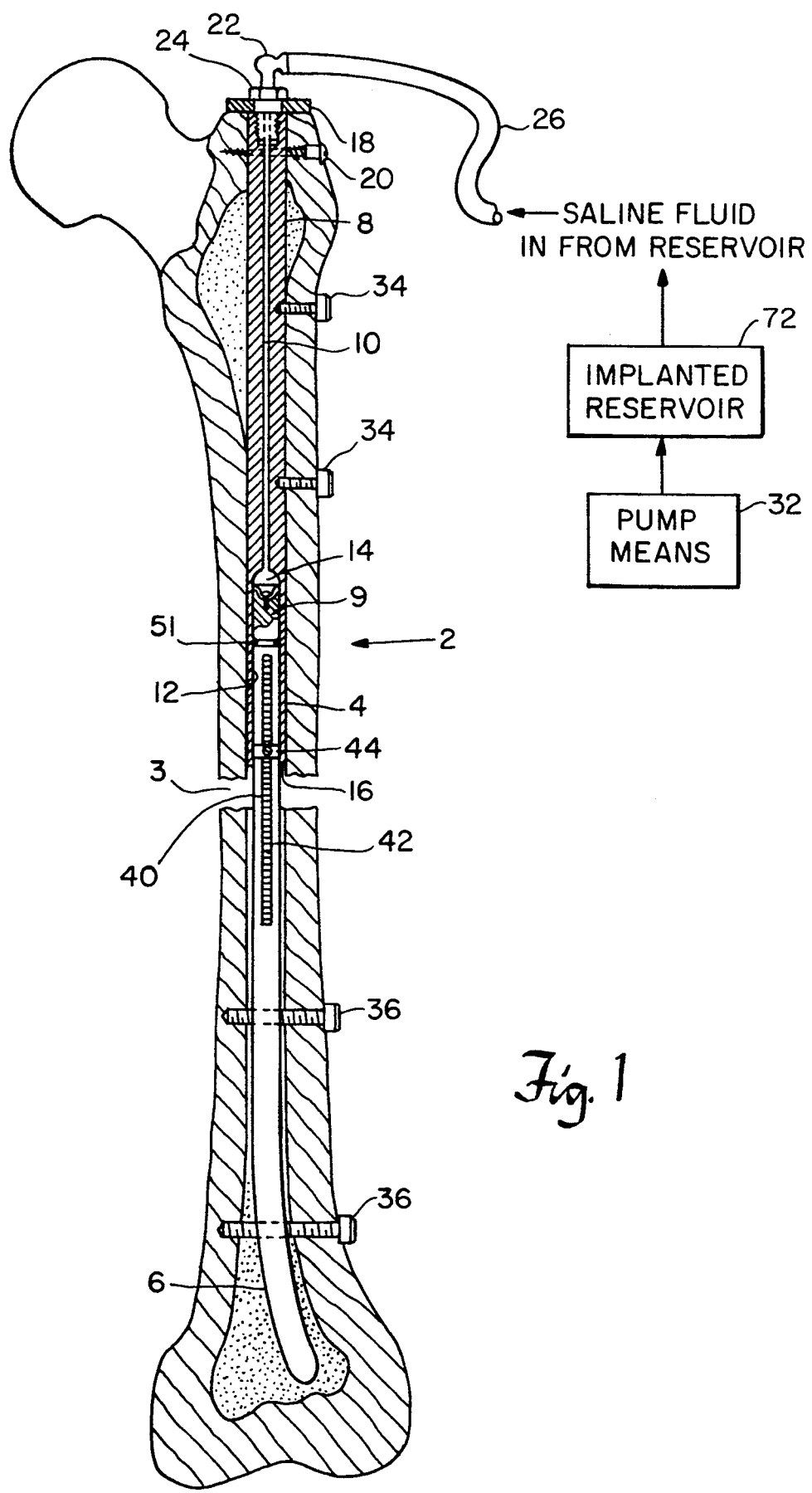
FIG. 1 is a sectional view of a bone lengthening device embodying the present invention and which is located in the femur.

A device for lengthening bone and soft tissue in a human or other animal by incrementally extending the distance between discrete separated portions of the bone or tissue to permit continued growth between the portions will be seen in FIG. 1. The device is shown inserted into a human femur 2, although it could be another bone in a human or animal. Initially, a surgeon removes the soft, pulpy material in the medullar canal to produce an elongate opening. He then cuts the bone transversely as at gap 3 to receive an intramedullary nail or rod generally designated 4.

The rod includes a distal portion 6 and a proximal portion 8. The proximal portion has formed in it a central bore 10 which leads to a cylinder 12 having an upper, domed shaped, fluid chamber 14. The proximal portion terminates at a point designated 16. A plate 18 is secured by screws 20 to the femur. A one-way valve 22 is threaded into the plate 18 and/or portion 8 and is secured by a nut 24 at the proximal end of the femur. A flexible conduit 26 leads from the one-way valve 22 to an implanted reservoir 72 (FIG. 1) which, in turn, is actuated by a pump means 32, both elements to be described in greater detail hereinafter. The proximal portion 8 of the intramedullary nail is secured to the femur by screws 34. The distal portion 6 of the intramedullary nail is secured by screws 36 within the distal portion of the medullar canal and on its upper end is formed a piston 9. Ratchet teeth 40 are formed in a line 42 in the piston 9.

A collar 44 is secured to the piston 9 by screws 48 and is received within an annular groove in the cylinder 12. A dog 46 is received within a slot 49 in the collar 44 for movement inwardly and outwardly radially with regard to the piston and has teeth 50 engagable with the mating teeth 40 formed in the piston 9. A fluid tight gasket 51 is fitted in a groove in the piston 9 and engages the wall of the cylinder 12. An annular, elastomeric shock absorbing element 52 is engagable with the collar 44 and the top 55 of the annular groove.

Lost motion between the piston 9 and the cylinder 12 occurs to the extent of the gap 54 between the collar 44 and the annular groove as the patient's lower leg is moved, thus causing the lower cut portion of the femur to move or vibrate slightly relative to the upper cut portion. In other words, the piston is permitted a small amount of lost motion relative to the cylinder, buffered by the shock absorber 52, which motion or vibration is beneficial to bone growth.

The dog 46 is urged to the left as seen in FIG. 3 by a compression spring 56 which is received within the collar 44. When the piston 9 and, hence, the distal portion of the bone, is urged downwardly by pressurized fluid entering the chamber 14, the dog 46 is moved slightly to the right as viewed in FIG. 3 by the teeth 40. Each tooth moves downwardly engaging the next adjacent tooth. This limits the motion of the distal end of the nail relative to the proximal portion to one direction. Thus, the piston can only move out of the cylinder upon admission of pressurized fluid to the chamber 14 above the piston head and not reverse direction. This will be done by the surgeon when the bone growth is completed.

An elastomeric piston cap 60 (FIG. 2) is secured by a screw 62 to the top of the piston member 9. The edges of the cap 62 maintain a seal against the inner wall 64 of the cylinder 12 which in conjunction with the annular seal 51 assures that there is no leakage of the saline operating fluid.

Pump means 32 and reservoir 72 will now be described referring next to FIG. 7 There will be seen an implantable supply of saline operating fluid 70 contained within an elastomeric diaphragm reservoir 72, implanted and secured by sutures 74 on an inner portion of the skin and muscle of the patient generally indicated 76. A ferromagnetic disk 78 is secured in an upper domed portion 73 of the diaphragm reservoir. The implanted conduit 26 which leads to the one-way valve 22 of the cylinder communicates with an opening 80 in the fluid reservoir 72.

An external pump exciting member 82 is engagable with the skin adjacent the ferromagnetic disk 78. It comprises an electromagnet 84, a battery 86 and a trigger 88 such that a surgeon or even a patient can trigger the exciting member to cause the ferromagnetic disk 78 to pulse toward and away from the electromagnet 84 to compress and relax the diaphragm reservoir to cause the saline fluid to pass through the conduit 26 through the one-way valve 22 and into the domed chamber 14 at the top of the piston.

An alterative pump means 32a and reservoir 72a is shown in FIG. 8. The reservoir 72a is connected by a flexible conduit 26a to a pump 90 operated from a reversible geared motor 92. A programmable microprocessor 94, through batteries 96, supplies signal to the motor 92 to pump fluid from the reservoir 72a through conduit 26b into the upper domed chamber 14 of the cylinders 12. The motor 92, being reversible, may also pump fluid back to the reservoir 72a.

Figure 4:
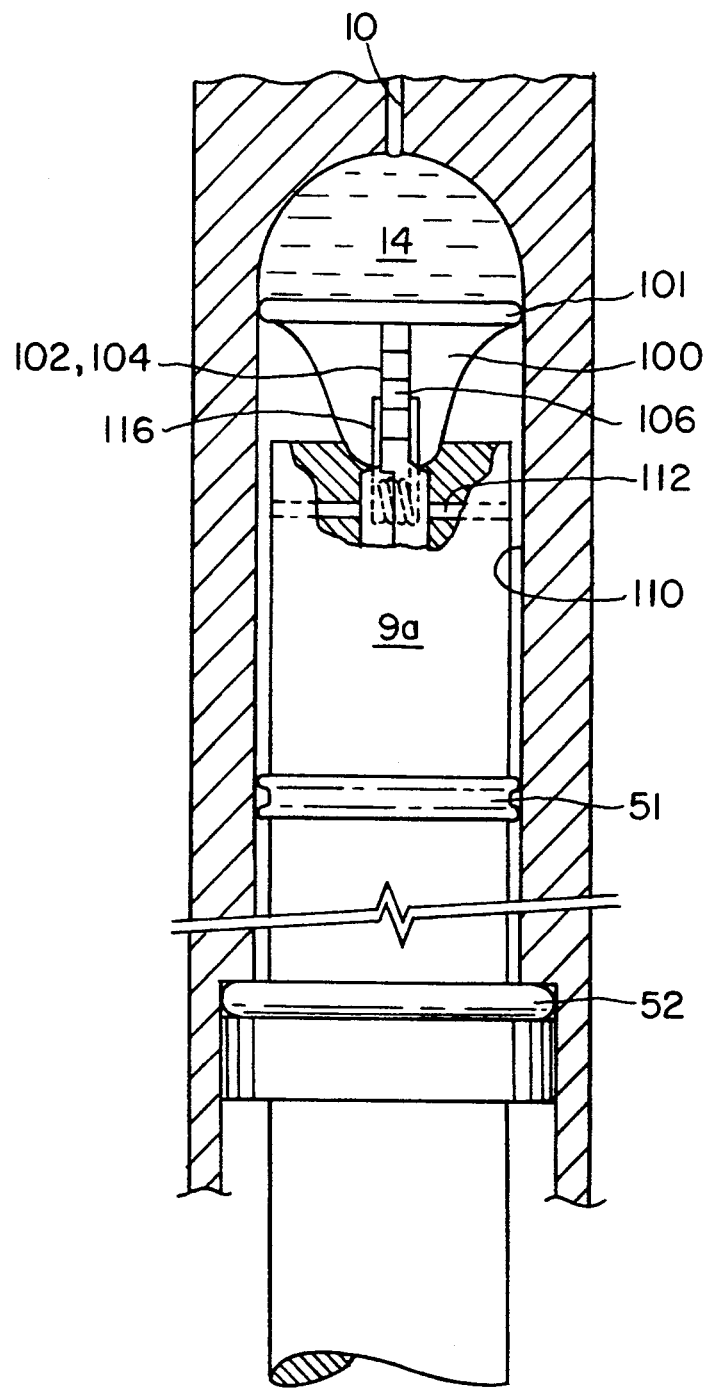
FIGS. 4, 5 and 6 are detailed enlarged views of an alternative embodiment of the racheting mechanism including means for reversing the direction of the mechanism.
Figure 5:
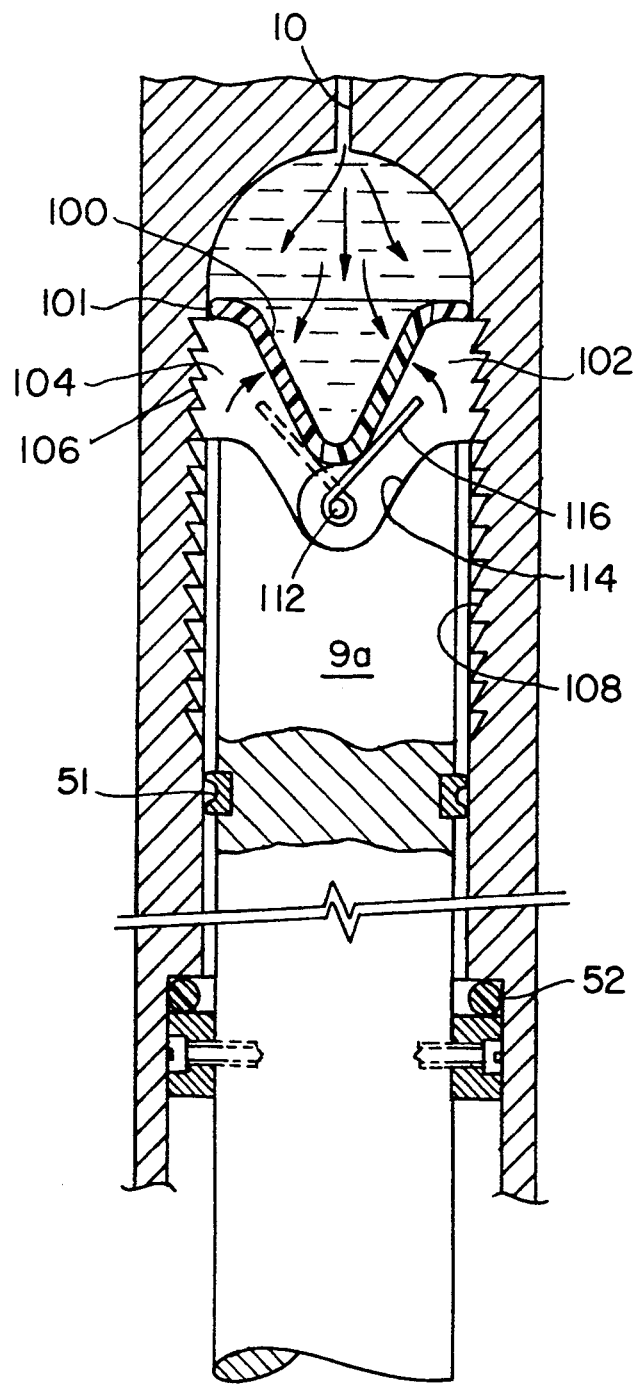
Figure 6:
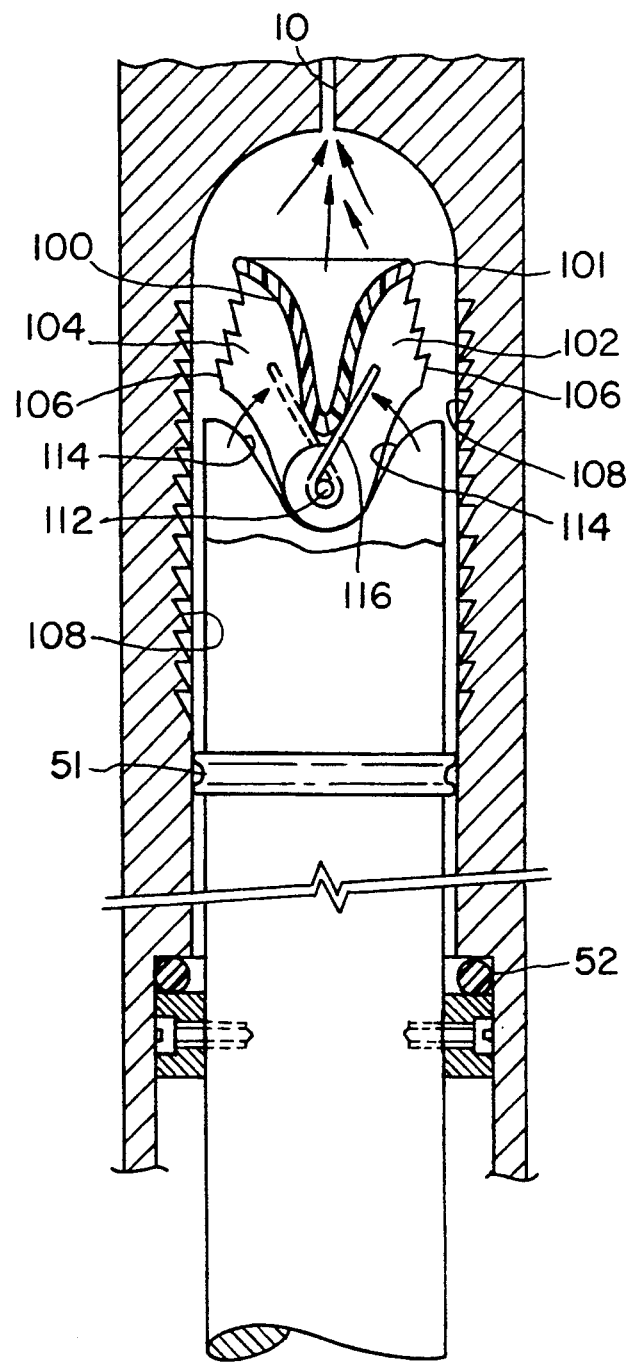

With reference to FIGS. 4, 5 and 6, mechanism for reversing the direction of the piston 9a within the cylinder will now be described. At the top of the piston, an inverted, bell shaped seal 100 is provided which is mounted for flexure between a pair of hinged racheting wings 102, 104, having teeth 106 which are engagable with mating teeth 108 on the interior of the cylinder wall. The wings 102, 104 are pivoted on a rod 112 received within bores in the top of the piston 9a. The piston is cut away at 114 to accommodate the lower ends of the wings which pivot inwardly and outwardly under the control of a coiled spring 116.

When it is desired to incrementally separate the proximal and distal portions of the bone, the implantable reservoir 72 is pressurized either externally by the electromagnet 82 or, preferably, the reservoir 72a is pressurized by the microprocessor operated pump 90 because the system is reversible. This causes fluid to flow through the flexible tube through the passageway 10 into the upper domed chamber 14 of the cylinder. The pressurized fluid acts against the seal 100 expanding its upper annular portion 101 to expand against the cylinder walls as shown in FIGS. 4 and 5. The pressure urges the wings 102, 104 apart against the force of its spring 116. The teeth 106 engage the teeth 108 in the cylinder walls, one by one. Continued pressurization urges the piston 9a downwardly causing the bones to separate and permit new growth to take place.

If, for some reason, the bone portions have been separated too much or it is desired to terminate the bone growth, depressurization of the fluid above the piston permits the coiled spring 116 to squeeze the seal 100 together as shown in FIG. 6 with the pressurized saline fluid reversing direction in the passageway 10 and returning to the reservoir 72a. The reversible pump 90 controls the fluid reversal.

Without using the pump 90, with the teeth 106 on the wings 102, 104 withdrawn from the teeth 108 on the inner cylinder walls, pressure on the distal end of the bone, as for example, by the orthopedist applying counter pressure, can cause the piston 9a and the distal end of the bone to rise slightly, closing the gap 3 between it and the proximal portion of the bone.

What is claimed is:

1. A device insertable in the medullar canal of a bone for lengthening the bone and tissue in a human or animal by incrementally extending the distance between discrete portions of the bone which are separated into a proximal portion and a distal portion to permit continued growth between the separated portions comprising:

an intramedullary nail having a distal portion and a proximal portion;

the proximal portion of the nail being securable within the medullar canal or the bone at the proximal end of the bone;

the distal portion of the nail being securable within the medullar canal of the bone at the distal end of the bone;

a hydraulic cylinder connected to the proximal portion of the nail;

a piston connected to the distal portion of the nail and movable in the cylinder;

a supply of operating fluid contained within an implantable elastomeric diaphragm in communication with the cylinder; and racheting mechanism between the piston and cylinder to limit the relative movement of the proximal and distal portions of the intramedullary nail and the bone portions to which they are securable to one direction.

2. Device according to claim 1 wherein the implantable elastomeric diaphragm includes a ferromagnetic member and external electromagnetic means for exciting said ferromagnetic member to pulse and compress and relax the diaphragm to cause the operating fluid to pass into the cylinder.

3. Device according to claim 1 wherein the operating fluid is saline.

4. Device according to claim 1 wherein the ratcheting mechanism comprises a spring-biased, toothed, dog secured to the cylinder which is engagable with a toothed ratchet on the piston.

5. Device according to claim 1 wherein the ratcheting mechanism comprises a pair of spring-biased, toothed, wings on the piston which are engagable with a pair of toothed racks in the cylinder wall.

6. A device insertable in the medullar canal of a bone for lengthening the bone and tissue in a human or animal by incrementally extending the distance between discrete portions of the bone which are separated into a proximal portion and a distal portion to permit continued growth between the separated portions comprising:

an intramedullary nail having a distal portion and a proximal portion;

the proximal portion of the nail being securable within the medullar canal of the bone at the proximal end of the bone;

the distal portion of the nail being securable within the medullar canal of the bone at the distal end of the bone;

a hydraulic cylinder connected to the proximal portion of the nail;

a piston connected to the distal portion of the nail and movable in the cylinder;

a supply of operating fluid, in communication with the cylinder;

a shock absorbing element operatively engagable with both the piston and the cylinder; and mechanism for permitting limited reciprocal lost motion in the direction of movement of the piston between the piston and the cylinder buffered by the shock absorbing element to permit the distal portion of the femur to move and vibrate slightly relative to the proximal portion to stimulate bone growth between the separated portions of the bone.

7. Device according to claim 2 wherein the supply of operating fluid communicates with pump means for pumping the fluid to the cylinder.

8. Device according to claim 6 wherein the supply of operating fluid is contained in an implantable elastomeric diaphragm reservoir and is operated by an external pump.

9. Device according to claim 6 wherein the operating fluid is saline.

10. Device according to claim 6 wherein the ratcheting mechanism comprises a spring-biased, toothed, dog secured to the cylinder which is engagable with a toothed ratchet on the piston.

11. A device insertable in the medullar canal of a bone for lengthening the bone and tissue in a human or animal by incrementally extending the distance between discrete portions of the bone which are separated into a proximal portion and a distal portion to permit continued growth between the separated portions comprising:

an intramedullary nail having a distal portion and a proximal portion;

the proximal portion of the nail being securable within the medullar canal of the bone at the proximal end of the bone;

the distal portion of the nail being securable within the medullar canal of the bone at the distal end of the bone;

a hydraulic cylinder connected to the proximal portion of the nail;

a piston connected to the distal portion of the nail and movable in the cylinder;

a supply of operating fluid in communication with the cylinder;

racheting mechanism between the piston and cylinder to limit their relative movement and that of the bone portions to which they are secured to one direction; and mechanism responsive to depressurization of the operating fluid for releasing the ratcheting mechanism to permit the piston to reverse direction relative to the cylinder.

12. Device according to claim 3 wherein the supply of operating fluid communicates with pump means for pressurizing and depressurizing the fluid.

13. Device according to claim 11 wherein the supply of operating fluid is contained in an implantable elastomeric diaphragm and is operated by pump means.

14. Device according to claim 11 wherein the operating fluid is saline.

15. Device according to claim 11 wherein the ratcheting mechanism comprises a pair of spring-biased, toothed, wings on the piston which are engagable with a pair of toothed racks in the cylinder wall.

* * * * *